United States Patent [19]

Petusky

[11] Plant 5,017

[45] Mar. 29, 1983

[54] CHRYSANTHEMUM PLANT (LIMELIGHT)

[76] Inventor: Kerry S. Petusky, 28 W. 748 Barnes Ave., West Chicago, Ill. 60185

[21] Appl. No.: 221,401

[22] Filed: Jan. 8, 1981

[51] Int. Cl.[3] ..... A01H 5/00

[52] U.S. Cl. ..... Plt./74

[58] Field of Search ..... Plt./74

*Primary Examiner*—Robert E. Bagwill

[57] ABSTRACT

A new cultivar of pot chrysanthemum characterized by its single flower form of medium size and white coloration, its abundant production of blooms when grown as a spray pot, its minimal pollen production, its vigorous and upright growth habit with abundant foliage, its nine-week photoperiodic response, and its ability for year around flowering on medium treatment.

1 Drawing Figure

BACKGROUND OF THE NEW PLANT

My new variety of pot chrysanthemum was selected by me from a population of seedlings resulting from the hybridization of the variety 'Bonnie Jean' with the variety 'Garland' (U.S. Plant Pat. No. 3,576) with the objective of creating new and unusual varieties. This hybridization was performed by me during March 1976, seeds were then harvested and sown and flowered October 1976. From this population of flowering seedlings, this new plant was selected by me and asexually reproduced under my direction and further propagated by means of vegetative cuttings. This work was performed in greenhouses at West Chicago, Ill.

Through successive generations of asexual reproduction, this plant has proved that its distinctive characteristics are firmly fixed and hold true from generation to generation.

DESCRIPTION OF THE DRAWINGS

My new chrysanthemum variety is illustrated by the accompanying full color photographic rendition showing the new variety as it appears as a fully grown potted plant, the colors shown being as nearly true as it is reasonably possible to obtain by conventional photographic procedures.

DESCRIPTION OF THE NEW PLANT

The following is a detailed description of my new variety of chrysanthemum, the color designations being according to the R.H.S. Colour Chart published by The Royal Horticultural Society of London, England.

THE PLANT

Origin: Seedling.

Parentage: Bonnie Jean × Garland (U.S. Plant Pat. No. 3,576).

Classification:

*Botanic.*—*Chrysanthemum morifolium.*

*Commercial.*—Greenhouse pot plant.

Form: Vase-shaped, perennial herbaceous bush.

Height: Varies with cultural practices.

Growth: Upright and vigorous, sturdy, with good strength.

Branching: Normal under natural conditions.

Foliage:

*Quantity.*—Abundant, 8 to 11 leaves on 10 cm. of stem.

*Leaf size.*—Length — Approximately 7.5 to 13 cm. (typical mature leaf). Width — Approximately 4.5 to 9.0 cm. (typical mature leaf).

*Shape.*—Lobed, deeply cleft and serrated.

*Texture.*—Canescent.

*Color.*—Upper side — 147A. Under side — 147B.

*Venation.*—Pinnate.

*Petioles.*—Length — Approximately 2.0 to 4.0 cm.

THE BUD

Form: Globular.

Size: Varies in both diameter and depth.

Opening rate: Slow, typical chrysanthemum.

Color:

*When phyllaries first divide.*—155A.

*When phyllaries begin to unfurl.*—155A.

Phyllaries: Many involucral, upstanding bracts on the outside of the receptacle.

*Shape.*—Spear-shaped.

*Color.*—Inside — 138A. Outside — 137B.

*Surface texture.*—Pubescent.

Peduncle: Sturdy and erect.

*Length.*—Varies considerably.

*Surface texture.*—Canescent.

*Color.*—138B.

THE FLOWER

Response: 9 week.

Recommended flowering: Year around with photoperiodic control.

Bloom:

*Type.*—Single and composit.

*Borne.*—A head of many florets borne on a receptacle.

*Shape.*—Cup-shaped when bloom first opens, becoming almost flat upon maturation.

*Size.*—Medium-size bloom. Diameter — Approximately 6.0 to 7.8 cm. Depth — Approximately 1.3 to 1.8 cm.

Florets: Quantity — numerous.

*Form.*—Linear with obtuse apex.

*Firmness.*—Soft.

*Appearance.*—Very slight shine.

*Color.*—Ray florets — Upper side: 155A, 155B, 155D. Reverse side: 155A, 155B, 155D. Disc florets — 151A. Discoloration: No change as full bloom ages. Occasional linear yellow (5B, 5C) streaks approximately 0.3 to 1.5 mm. in width appear in ray florets.

Persistence: Flowers hang on and dry.
Lasting quality:
*On plant.*—4 weeks. Not recommended for cut-flower use.

REPRODUCTIVE ORGANS

Stamens:
*Quantity.*—5 to each disc floret.
*Arrangement.*—Syngenesious.
*Filaments.*—Length — 2 to 4 mm. Color — yellow.
*Pollen.*—Color — yellow.
Pistils:
*Number.*—One to each ray and disc floret.
*Styles.*—Length — 4 to 5 mm.
*Stigmas.*— *Color — yellowish-green.*
Ovaries: Inferior bicarpellate.

This new variety of chrysanthemum is particularly characterized by its single flower form with creamy white ray florets which occasionally exhibit a yellow streak and disc florets which are initially greenish-yellow, gradually becoming more yellow as the bloom matures. Disc florets produce very minimal pollen. Ray florets do not reflex upon maturation.

This plant is also characterized by its upright pot habit; its abundant dark green foliage; its very abundant production of blooms when grown as a spray pot; and its ability to be flowered year around, the plant flowering approximately nine weeks from the commencement of short-day treatment.

Its primary use is for six-inch, year around pot production.

I claim:

1. A new and distinctive cultivar of chrysanthemum, substantially as herein shown and described, particularly characterized by its single flower form, generally white coloration of the ray florets, greenish-yellow coloration of the disc florets, and its very floriferous and vigorous growth habit.

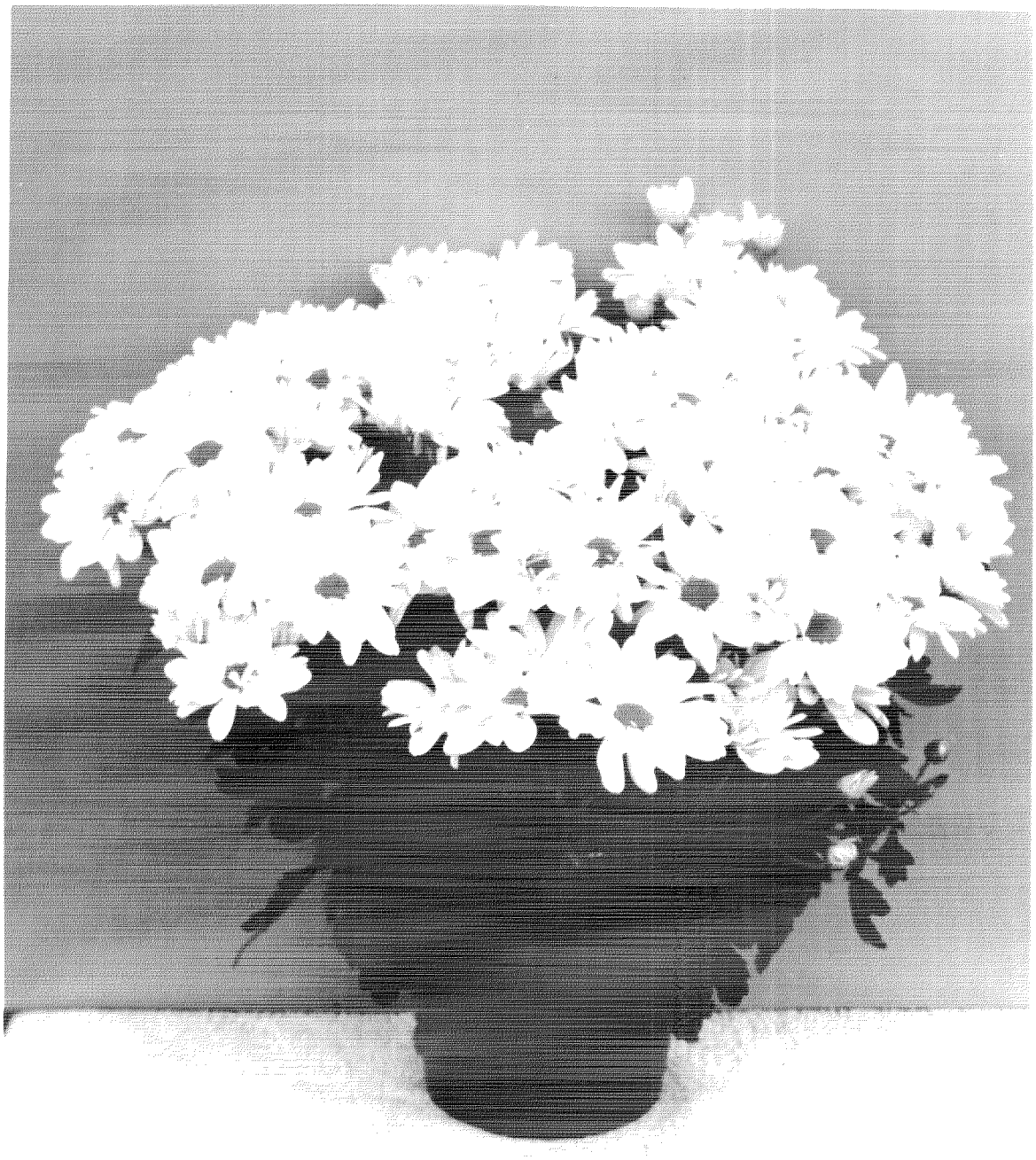

* * * * *